(12) United States Patent
Rush et al.

(10) Patent No.: US 8,343,092 B2
(45) Date of Patent: ***Jan. 1, 2013

(54) METHOD AND SYSTEM FOR PROVIDING INTEGRATED MEDICATION INFUSION AND ANALYTE MONITORING SYSTEM

(75) Inventors: Benjamin M. Rush, Oakland, CA (US); Christopher V. Reggiardo, Castro Valley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 12/625,518

(22) Filed: Nov. 24, 2009

(65) Prior Publication Data

US 2010/0076412 A1    Mar. 25, 2010

Related U.S. Application Data

(63) Continuation of application No. 11/386,915, filed on Mar. 21, 2006.

(60) Provisional application No. 60/664,215, filed on Mar. 21, 2005.

(51) Int. Cl.
*A61M 31/00* (2006.01)
(52) U.S. Cl. .......................................... 604/65; 604/503
(58) Field of Classification Search .................... 604/65, 604/66, 503, 504
See application file for complete search history.

(56) References Cited

U.S. PATENT DOCUMENTS

| | | | |
|---|---|---|---|
| 2,508,253 | A | 5/1950 | Haggardt |
| 2,915,579 | A | 12/1959 | Mendelsohn |
| 3,374,337 | A | 3/1968 | Burley |
| 3,510,747 | A | 5/1970 | Petrides |
| 3,541,892 | A | 11/1970 | Kubinek et al. |
| 3,606,592 | A | 9/1971 | Madurski et al. |
| 3,750,687 | A | 8/1973 | Williams |
| 3,843,455 | A | 10/1974 | Bier |
| 3,923,060 | A | 12/1975 | Elinwood |
| 3,930,493 | A | 1/1976 | Williamson |
| 3,938,140 | A | 2/1976 | Garcia et al. |
| 3,994,799 | A | 11/1976 | Yao et al. |
| 4,018,547 | A | 4/1977 | Rogen |
| 4,048,551 | A | 9/1977 | Bosik |
| 4,121,282 | A | 10/1978 | Ohsawa |
| 4,146,029 | A | 3/1979 | Elinwood |
| 4,193,397 | A | 3/1980 | Tucker et al. |
| 4,268,173 | A | 5/1981 | Barnard et al. |
| 4,288,793 | A | 9/1981 | Lotscher |

(Continued)

FOREIGN PATENT DOCUMENTS

EP        0455455        11/1991

(Continued)

OTHER PUBLICATIONS

Abstract of Japanese Publication No. JP-2001-077423, Published Mar. 23, 2001.

(Continued)

*Primary Examiner* — Kevin C Sirmons
*Assistant Examiner* — Deanna K Hall
(74) *Attorney, Agent, or Firm* — Jackson & Co., LLP

(57) ABSTRACT

Method and system for integrating infusion device and analyte monitoring system including medication infusion device such as an insulin pump and an analyte monitoring system such as a glucose monitoring system are provided.

34 Claims, 8 Drawing Sheets

U.S. PATENT DOCUMENTS

| | | | |
|---|---|---|---|
| 4,309,156 A | 1/1982 | Gonner et al. |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Bush et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,264,104 A | 11/1993 | Gregg et al. |
| 5,267,026 A | 11/1993 | Kawahara et al. |
| 5,278,997 A | 1/1994 | Martin |
| 5,284,423 A | 2/1994 | Holdsworth et al. |
| 5,284,425 A | 2/1994 | Holtermann et al. |
| 5,291,614 A | 3/1994 | Baker et al. |
| 5,291,887 A | 3/1994 | Stanley et al. |
| 5,320,725 A | 6/1994 | Gregg et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A | 5/1996 | Benton |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,573,506 A | 11/1996 | Vasko |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,665,222 A | 9/1997 | Heller et al. |
| 5,671,301 A | 9/1997 | Kuperschmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,738,220 A | 4/1998 | Geszler |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,812,102 A | 9/1998 | Sprole et al. |
| 5,814,020 A | 9/1998 | Gross |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,856,631 A | 1/1999 | Julien |
| 5,858,001 A | 1/1999 | Tsals et al. |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,919,167 A | 7/1999 | Mulhauser |
| 5,923,512 A | 7/1999 | Brownlow et al. |
| 5,931,814 A | 8/1999 | Gross et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |

| Patent No. | Date | Inventor |
|---|---|---|
| 5,965,380 A | 10/1999 | Heller et al. |
| 5,968,011 A | 10/1999 | Larsen et al. |
| 5,971,922 A | 10/1999 | Arita et al. |
| 5,972,199 A | 10/1999 | Heller et al. |
| 5,993,411 A | 11/1999 | Choi |
| 5,994,878 A | 11/1999 | Ostergaard et al. |
| 5,997,501 A | 12/1999 | Gross et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |
| 6,067,017 A | 5/2000 | Stewart et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A | 6/2000 | Helstab et al. |
| 6,077,660 A | 6/2000 | Wong et al. |
| 6,081,104 A | 6/2000 | Kern |
| 6,083,710 A | 7/2000 | Heller et al. |
| 6,085,871 A | 7/2000 | Karamata |
| 6,086,575 A | 7/2000 | Mejslov |
| 6,091,975 A | 7/2000 | Daddona et al. |
| 6,093,156 A | 7/2000 | Cunningham et al. |
| 6,093,172 A | 7/2000 | Funderburk et al. |
| 6,103,033 A | 8/2000 | Say et al. |
| 6,120,676 A | 9/2000 | Heller et al. |
| 6,121,009 A | 9/2000 | Heller et al. |
| 6,129,823 A | 10/2000 | Hughes et al. |
| 6,132,371 A | 10/2000 | Dempsey et al. |
| 6,134,461 A | 10/2000 | Say et al. |
| 6,142,939 A | 11/2000 | Eppstein et al. |
| 6,143,164 A | 11/2000 | Heller et al. |
| 6,144,303 A | 11/2000 | Federman |
| 6,144,869 A | 11/2000 | Berner et al. |
| 6,144,922 A | 11/2000 | Douglas et al. |
| 6,147,342 A | 11/2000 | Kucher |
| 6,154,855 A | 11/2000 | Norman |
| 6,155,992 A | 12/2000 | Henning et al. |
| 6,157,442 A | 12/2000 | Raskas |
| 6,160,449 A | 12/2000 | Klomsdorf et al. |
| 6,162,202 A | 12/2000 | Sicurelli et al. |
| 6,162,611 A | 12/2000 | Heller et al. |
| 6,164,284 A | 12/2000 | Schulman et al. |
| 6,173,160 B1 | 1/2001 | Liimatainen |
| 6,175,752 B1 | 1/2001 | Say et al. |
| 6,180,416 B1 | 1/2001 | Kurnik et al. |
| 6,185,452 B1 | 2/2001 | Schulman et al. |
| 6,186,982 B1 | 2/2001 | Gross et al. |
| 6,201,980 B1 | 3/2001 | Darrow et al. |
| 6,203,288 B1 | 3/2001 | Kottke |
| 6,206,841 B1 | 3/2001 | Cunningham et al. |
| 6,208,894 B1 | 3/2001 | Schulman et al. |
| 6,212,416 B1 | 4/2001 | Ward et al. |
| 6,215,206 B1 | 4/2001 | Chitayat |
| 6,222,514 B1 | 4/2001 | DeLuca |
| 6,228,100 B1 | 5/2001 | Schraga |
| 6,232,370 B1 | 5/2001 | Kubota et al. |
| 6,233,471 B1 | 5/2001 | Berner et al. |
| 6,233,539 B1 | 5/2001 | Brown |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,283,951 B1 | 9/2001 | Flaherty et al. |
| 6,284,478 B1 | 9/2001 | Heller et al. |
| 6,288,653 B1 | 9/2001 | Shih |
| 6,293,925 B1 | 9/2001 | Safabash et al. |
| 6,295,506 B1 | 9/2001 | Heinonen et al. |
| 6,298,254 B2 | 10/2001 | Tamada |
| 6,298,255 B1 | 10/2001 | Cordero et al. |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,312,888 B1 | 11/2001 | Wong et al. |
| 6,315,721 B2 | 11/2001 | Schulman et al. |
| 6,326,160 B1 | 12/2001 | Dunn et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,368,141 B1 | 4/2002 | Van Antwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,894 B1 | 4/2002 | Deweese et al. |
| 6,379,301 B1 | 4/2002 | Worthington et al. |
| 6,381,496 B1 | 4/2002 | Meadows et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,418,332 B1 | 7/2002 | Mastrototaro et al. |
| 6,419,642 B1 | 7/2002 | Marchitto et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,442,413 B1 | 8/2002 | Silver |
| 6,445,374 B2 | 9/2002 | Albert et al. |
| 6,461,329 B1 | 10/2002 | Van Antwerp et al. |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,475,196 B1 | 11/2002 | Vachon |
| 6,478,736 B1 | 11/2002 | Mault |
| 6,480,730 B2 | 11/2002 | Darrow et al. |
| 6,482,158 B2 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,485,138 B1 | 11/2002 | Kubota et al. |
| 6,485,461 B1 | 11/2002 | Mason et al. |
| 6,485,465 B2 | 11/2002 | Morberg et al. |
| 6,492,180 B2 | 12/2002 | Brown et al. |
| 6,498,043 B1 | 12/2002 | Schulman et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |

| | | |
|---|---|---|
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnacaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,980 B2 | 12/2003 | Morberg et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,789,195 B1 | 9/2004 | Prihoda et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 | 8/2005 | Klemm |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stirovic et al. |
| 7,024,245 B2 | 4/2006 | Lebel et al. |
| 7,024,249 B2 | 4/2006 | Weisner et al. |

| | | |
|---|---|---|
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,058,437 B2 | 6/2006 | Buse et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,193,521 B2 | 3/2007 | Morberg et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,283,867 B2 | 10/2007 | Strother et al. |
| 7,291,497 B2 | 11/2007 | Holmes et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,323,091 B1 | 1/2008 | Gillette et al. |
| 7,324,949 B2 | 1/2008 | Bristol et al. |
| 7,343,188 B2 | 3/2008 | Sohrab |
| 7,364,592 B2 | 4/2008 | Carr-Brendel et al. |
| 7,366,556 B2 | 4/2008 | Brister et al. |
| 7,371,247 B2 | 5/2008 | Boeker et al. |
| 7,379,765 B2 | 5/2008 | Petisce et al. |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,679,407 B2 | 3/2010 | Reggiardo |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,181 B2 | 6/2010 | Rush et al. |
| 7,753,873 B2 | 7/2010 | Rush |
| 7,753,874 B2 | 7/2010 | Rush et al. |
| 7,756,561 B2 | 7/2010 | Reggiardo et al. |
| 7,766,864 B2 | 8/2010 | Rush et al. |
| 7,768,408 B2 | 8/2010 | Reggiardo et al. |
| 7,778,795 B2 | 8/2010 | Fukushima et al. |
| 7,850,621 B2 | 12/2010 | Briggs et al. |
| 7,882,611 B2 | 2/2011 | Shah et al. |
| 7,884,729 B2 | 2/2011 | Reggiardo et al. |
| 7,911,010 B2 | 3/2011 | Stetter |
| 7,954,385 B2 | 6/2011 | Raisanen |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0034617 A1 | 10/2001 | Kimata |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1 | 2/2002 | Watanabe et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0065682 A1 | 5/2002 | Goldenberg |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |

| | | |
|---|---|---|
| 2002/0169394 A1 | 11/2002 | Eppstein et al. |
| 2002/0169439 A1 | 11/2002 | Flaherty et al. |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0055380 A1 | 3/2003 | Flaherty et al. |
| 2003/0060692 A1 | 3/2003 | Ruchti et al. |
| 2003/0060765 A1 | 3/2003 | Campbell et al. |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnacaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0154405 A1 | 8/2003 | Harrison |
| 2003/0158472 A1 | 8/2003 | Sohrab |
| 2003/0158707 A1 | 8/2003 | Doi |
| 2003/0167035 A1 | 9/2003 | Flaherty et al. |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0030226 A1 | 2/2004 | Quy |
| 2004/0039256 A1 | 2/2004 | Kawatahara et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0059284 A1 | 3/2004 | Nash et al. |
| 2004/0064088 A1 | 4/2004 | William et al. |
| 2004/0064096 A1 | 4/2004 | Flaherty et al. |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0116847 A1 | 6/2004 | Wall |
| 2004/0116866 A1 | 6/2004 | William et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0153032 A1 | 8/2004 | Garribotto et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0254884 A1 | 12/2004 | Haber et al. |
| 2004/0263354 A1 | 12/2004 | Mann et al. |
| 2004/0264396 A1 | 12/2004 | Ginzburg et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |

| | | |
|---|---|---|
| 2005/0118726 A1 | 6/2005 | Scultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0218880 A1 | 10/2005 | Ioffe |
| 2005/0235732 A1 | 10/2005 | Rush |
| 2005/0238503 A1 | 10/2005 | Rush et al. |
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0249506 A1 | 11/2005 | Fuse |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0004603 A1 | 1/2006 | Peterka et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartowiak et al. |
| 2006/0074564 A1 | 4/2006 | Bartkowiak et al. |
| 2006/0094986 A1 | 5/2006 | Neel et al. |
| 2006/0154642 A1 | 7/2006 | Scannell |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0253085 A1 | 11/2006 | Geismar et al. |
| 2006/0253086 A1 | 11/2006 | Moberg et al. |
| 2006/0273759 A1 | 12/2006 | Reggiardo |
| 2006/0282290 A1 | 12/2006 | Flaherty et al. |
| 2006/0293577 A1 | 12/2006 | Morrison et al. |
| 2007/0016381 A1 | 1/2007 | Kamath et al. |
| 2007/0032717 A1 | 2/2007 | Brister et al. |
| 2007/0078323 A1 | 4/2007 | Reggiardo et al. |
| 2007/0078818 A1 | 4/2007 | Zvitz et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0163880 A1 | 7/2007 | Woo et al. |
| 2007/0173711 A1 | 7/2007 | Shah et al. |
| 2007/0176867 A1 | 8/2007 | Reggiardo et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0071156 A1 | 3/2008 | Brister et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097918 A1 | 4/2008 | Spector et al. |
| 2008/0103447 A1 | 5/2008 | Reggiardo et al. |
| 2008/0108942 A1 | 5/2008 | Brister et al. |
| 2008/0119703 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0242961 A1 | 10/2008 | Brister et al. |
| 2008/0257063 A1 | 10/2008 | Rush et al. |
| 2008/0262469 A1 | 10/2008 | Brister et al. |
| 2008/0267787 A1 | 10/2008 | Rush et al. |
| 2008/0275313 A1 | 11/2008 | Brister et al. |
| 2008/0287764 A1 | 11/2008 | Rasdal et al. |

| | | |
|---|---|---|
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063196 A1 | 3/2009 | Frederickson |
| 2009/0063402 A1 | 3/2009 | Hayter |
| 2009/0068954 A1 | 3/2009 | Reggiardo et al. |
| 2009/0069750 A1 | 3/2009 | Schraga |
| 2009/0076355 A1 | 3/2009 | Reggiardo |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0105647 A1 | 4/2009 | Rush et al. |
| 2009/0105648 A1 | 4/2009 | Rush et al. |
| 2009/0105649 A1 | 4/2009 | Rush et al. |
| 2009/0112156 A1 | 4/2009 | Rush et al. |
| 2009/0112165 A1 | 4/2009 | Rush et al. |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163869 A1 | 6/2009 | Rush et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0216553 A1 | 8/2009 | Cellura |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0008794 A1 | 1/2010 | Rush et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0019721 A1 | 1/2010 | Reggiardo |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0049130 A1 | 2/2010 | Rush et al. |
| 2010/0049131 A1 | 2/2010 | Rush et al. |
| 2010/0049132 A1 | 2/2010 | Rush et al. |
| 2010/0049133 A1 | 2/2010 | Rush et al. |
| 2010/0057007 A1 | 3/2010 | Rush et al. |
| 2010/0057038 A1 | 3/2010 | Rush et al. |
| 2010/0063373 A1 | 3/2010 | Kamath et al. |
| 2010/0063446 A1 | 3/2010 | Rush et al. |
| 2010/0063449 A1 | 3/2010 | Rush et al. |
| 2010/0068072 A1 | 3/2010 | Rush et al. |
| 2010/0076283 A1 | 3/2010 | Simpson et al. |
| 2010/0076371 A1 | 3/2010 | Rush et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100041 A1 | 4/2010 | Rush et al. |
| 2010/0100042 A1 | 4/2010 | Rush et al. |
| 2010/0114028 A1 | 5/2010 | Rush et al. |
| 2010/0114029 A1 | 5/2010 | Rush et al. |
| 2010/0114073 A1 | 5/2010 | Rush et al. |
| 2010/0119693 A1 | 5/2010 | Tapsak et al. |
| 2010/0121169 A1 | 5/2010 | Petisce et al. |
| 2010/0241076 A1 | 9/2010 | Rush et al. |
| 2010/0241447 A1 | 9/2010 | Siniaguine et al. |
| 2010/0312177 A1 | 12/2010 | Rush et al. |

FOREIGN PATENT DOCUMENTS

| | | |
|---|---|---|
| EP | 0465708 | 1/1992 |
| EP | 0518524 | 12/1992 |
| EP | 0709573 | 5/1996 |
| EP | 0878707 | 11/1998 |
| EP | 0543916 | 7/2001 |
| EP | 1130638 | 9/2001 |
| EP | 0980688 | 12/2002 |
| EP | 1755443 | 11/2005 |
| EP | 1783536 | 5/2007 |
| FR | 2718492 | 10/1995 |
| JP | 1-080775 | 3/1989 |
| JP | 2001-177423 | 6/2001 |
| JP | 2001-056673 | 11/2001 |
| WO | WO-96/14026 | 5/1996 |
| WO | WO-96/34637 | 11/1996 |
| WO | WO-99/22236 | 5/1999 |
| WO | WO-99/56613 | 11/1999 |
| WO | WO-00/74753 | 12/2000 |
| WO | WO-01/41849 | 6/2001 |
| WO | WO-01/52727 | 7/2001 |
| WO | WO-01/54753 | 8/2001 |
| WO | WO-01/71186 | 9/2001 |
| WO | WO-02/39086 | 5/2002 |
| WO | WO-02/57627 | 7/2002 |
| WO | WO-02/058537 | 8/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-03/090509 | 4/2003 |

| | | | |
|---|---|---|---|
| WO | WO-03/053503 | | 7/2003 |
| WO | WO 03/071930 | * | 9/2003 |
| WO | WO-03/071930 | | 9/2003 |
| WO | WO-03/103763 | | 12/2003 |
| WO | WO-2004/028337 | | 4/2004 |
| WO | WO-2004/032994 | | 4/2004 |
| WO | WO-2004/061420 | | 7/2004 |
| WO | WO-2005/089103 | | 9/2005 |
| WO | WO-2005/101994 | | 11/2005 |
| WO | WO-2006/003919 | | 1/2006 |
| WO | WO-2006/079114 | | 7/2006 |
| WO | WO-2006/086701 | | 8/2006 |
| WO | WO-2006/102412 | | 9/2006 |
| WO | WO-2006/110913 | | 10/2006 |
| WO | WO-2006/113408 | | 10/2006 |
| WO | WO-2006/113521 | | 10/2006 |
| WO | WO-2006/118947 | | 11/2006 |
| WO | WO-2006/132884 | | 12/2006 |
| WO | WO-2007/041072 | | 4/2007 |
| WO | WO-2007/090037 | | 8/2007 |
| WO | WO-2008/055037 | | 5/2008 |
| WO | WO-2008/086541 | | 7/2008 |
| WO | WO-2008/110267 | | 9/2008 |

OTHER PUBLICATIONS

Chinese Patent Application No. 200680017650.0, English Translation & Original Language of Office Action mailed Jul. 6, 2011.
Chinese Patent Application No. 200680017650.0, English Translation of Office Action mailed Jul. 3, 2009.
Japanese Patent Application No. 2008-503129, English Translation & Original Language of Office Action mailed Apr. 19, 2011.
U.S. Appl. No. 12/643,970, Notice of Allowance mailed Jul. 29, 2011.
U.S. Appl. No. 12/643,970, Office Action mailed Dec. 22, 2010.
U.S. Appl. No. 12/643,971, Notice of Allowance mailed Aug. 1, 2011.
U.S. Appl. No. 12/643,971, Office Action mailed Dec. 22, 2010.
U.S. Appl. No. 12/643,971, Office Action mailed Jul. 5, 2011.
"An Electrochemical Slow Flow Meter", http://gore.ocean.washington.edu/research/slow_flow_meter.html, 2005, 3 pages.
Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.
Bard, A. J., et al., "Methods Involving Forced Convection—Hydrodynamic Methods", *Electrochemical Methods—Fundamentals and Applications*, 2001, pp. 331-367.
Kissinger, P. T., "Introduction to Analog Instrumentation", *Laboratory Techniques in Electroanalytical Chemistry, Second Edition, Revised and Expanded*, 1996, pp. 165-194.
Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.
PCT Application No. PCT/US2006/010403, International Preliminary Report on Patentability and Written Opinion of the International Searching Authority mailed Oct. 25, 2007.
PCT Application No. PCT/US2006/010403, International Search Report and Written Opinion of the International Searching Authority mailed Sep. 25, 2007.
U.S. Appl. No. 11/386,915, Office Action mailed Nov. 16, 2009.
U.S. Appl. No. 12/643,970, Office Action mailed Jun. 8, 2010.
U.S. App. No. 12/643,971, Office Action mailed Jun. 7, 2010.
Australian Patent Application No. 2006226988, Examiner's First Report mailed Sep. 14, 2010.
Chinese Patent Application No. 200680017650.0, English Translation of Second Office Action mailed May 20, 2010.
European Patent Application No. 06748550.8, Extended European Search Report mailed Jul. 2, 2008.
U.S. Appl. No. 11/386,915, Advisory Action mailed Oct. 25, 2010.
U.S. Appl. No. 11/386,915, Office Action mailed Jan. 31, 2012.

* cited by examiner

METHOD AND SYSTEM FOR PROVIDING INTEGRATED MEDICATION INFUSION AND ANALYTE MONITORING SYSTEM

RELATED APPLICATION

The present application is a continuation of U.S. patent application Ser. No. 11/386,915 filed Mar. 21, 2006, which claims priority under 35 USC §119(e) to provisional application No. 60/664,215 filed Mar. 21, 2005 and assigned to the assignee of the present application, the disclosure of each of which are incorporated herein in their entirety by reference for all purposes.

FIELD OF THE INVENTION

The present invention relates to methods and systems for integrating infusion systems and analyte monitoring systems. More specifically, the present invention relates to methods and systems for integrating insulin infusion devices with continuous analyte monitoring systems.

BACKGROUND OF THE INVENTION

Type 1 diabetics must periodically be administered with insulin to sustain their physiological conditions. Typically, these patients administer doses of either fast acting or slow acting insulin using needle type syringes, for example, prior to meals, and/or at a suitable time during the course of each day contemporaneously with the blood glucose level testing using fingerstick testing, for example. If insulin is not suitably administered, the diabetic patients risk serious if not fatal damage to the body.

Continued development and improvement in the external infusion pump therapy in recent years have drawn much appeal to the diabetic patients for, among others, improved management of diabetes by better regulating and controlling the intake of insulin. Typically, the patient inserts a cannula which is connected to an infusion tubing attached to an external pump, and insulin is administered based on preprogrammed basal profiles. Moreover, the external infusion devices presently available include computational capability to determined suitable bolus doses such as carbohydrate bolus and correction bolus, for example, to be administered in conjunction with the infusion device executing the patient's basal profile.

The basal profiles are generally determined by the patients' physician or caretaker and are based on a number of factors including the patient's insulin sensitivity and physiological condition which are diagnosed by the patient's physician, for example, and are typically intended to as accurately estimate the patient's glucose levels over a predetermined time period during which the patient is infusing insulin. The glucose levels may be estimated based on the patient's periodic discrete testing using a test strip and a blood glucose meter such as Freestyle® Glucose Meter available from Abbott Diabetes Care, Inc., of Alameda, Calif. Such estimations are, however, prone to error, and do not accurately mirror the patient's actual physiological condition.

SUMMARY OF THE INVENTION

In view of the foregoing, it would be desirable to have an integrated system combining the functionalities of an infusion device such as insulin infusion pumps, and analyte monitoring systems such as continuous glucose monitoring systems.

These and other objects, features and advantages of the present invention will become more fully apparent from the following detailed description of the embodiments, the appended claims and the accompanying drawings.

BRIEF DESCRIPTION OF THE FIGURES

FIG. 7A illustrates the integrated infusion device and monitoring system shown in FIG. 6 in further detail in one embodiment of the present invention, while

FIG. 11A illustrates a component perspective view of the infusion device cannula integrated with analyte monitoring system sensor electrodes in accordance with another embodiment of the present invention, while

DETAILED DESCRIPTION

Figure 1:
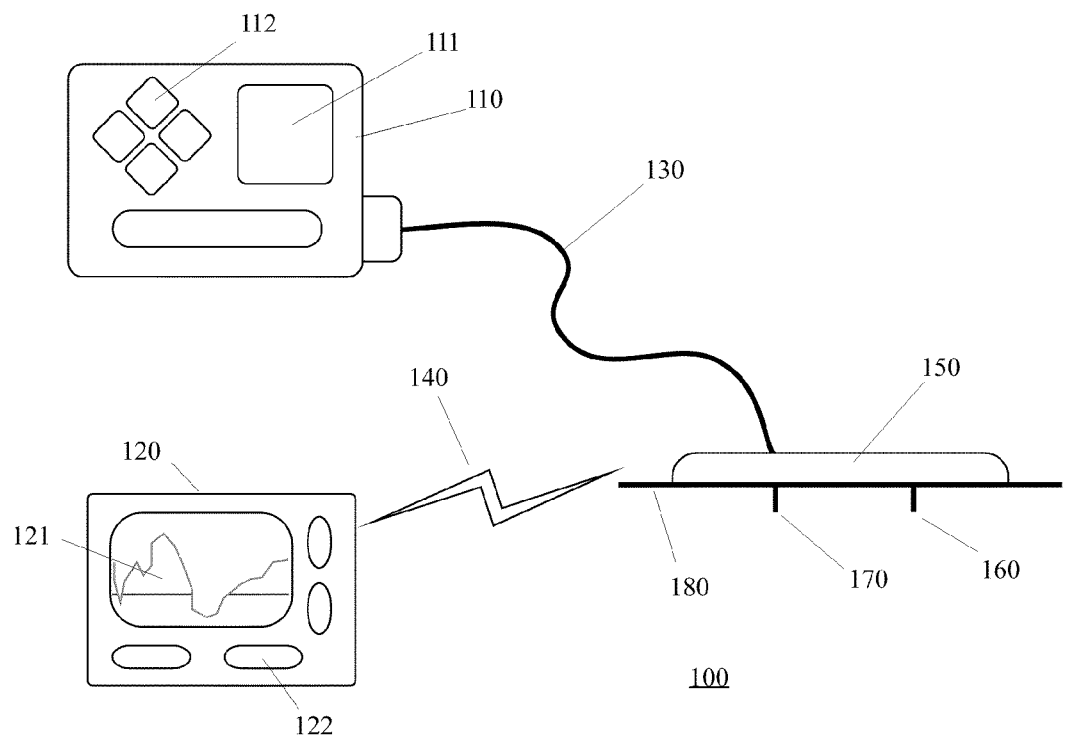
FIG. 1 illustrates an integrated infusion device and analyte monitoring system in accordance with one embodiment of the present invention.

FIG. 1 illustrates an integrated infusion device and analyte monitoring system in accordance with one embodiment of the present invention. Referring to FIG. 1, the integrated infusion device and analyte monitoring system 100 in one embodiment of the present invention includes an infusion device 110 connected to an infusion tubing 130 for liquid transport or infusion, and which is further coupled to a cannula 170. As can be seen from FIG. 1, the cannula 170 is configured to be mountably coupled to a transmitter unit 150, where the transmitter unit 150 is also mountably coupled to an analyte sensor 160. Also provided is an analyte monitor unit 120 which is configured to wirelessly communicate with the transmitter unit 150 over a communication path 140.

Referring to FIG. 1, in one embodiment of the present invention, the transmitter unit 150 is configured for unidirectional wireless communication over the communication path 140 to the analyte monitor unit 120. In one embodiment, the analyte monitor unit 120 may be configured to include a transceiver unit (not shown) for bi-directional communication over the communication path 140. The transmitter unit 150 in one embodiment may be configured to periodically and/or intermittently transmit signals associated with analyte levels detected by the analyte sensor 160 to the analyte monitor unit 120. The analyte monitor unit 120 may be configured to receive the signals from the transmitter unit 150 and in one embodiment, is configured to perform data storage and processing based on one or more preprogrammed or predetermined processes.

For example, in one embodiment, the analyte monitor unit 120 is configured to store the received signals associated with analyte levels in a data storage unit (not shown). Alternatively, or in addition, the analyte monitor unit 120 may be configured to process the signals associated with the analyte levels to generate trend indication by, for example, visual display of a line chart or an angular icon based display for output display on its display unit 121. Additional information may be output displayed on the display unit 121 of the analyte monitor unit 120 including, but not limited to, the substantially contemporaneous and real time analyte level of the patient received from the transmitter unit 150 as detected by the sensor 160. The real time analyte level may be displayed in a numeric format or in any other suitable format which provides the patient with the accurate measurement of the substantially real time analyte level detected by the sensor 160.

Additional analytes that may be monitored or determined by the sensor 160 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Referring back to FIG. 1, the sensor 160 may include a short term (for example, 3 day, 5 day or 7 day use) analyte sensor which is replaced after its intended useful life. Moreover, in one embodiment, the sensor 160 is configured to be positioned subcutaneous to the skin of the patient such that at least a portion of the analyte sensor is maintained in fluid contact with the patient's analyte such as, for example, interstitial fluid or blood. In addition, the cannula 170 which is configured to similarly be positioned under the patient's skin is connected to the infusion tubing 130 of the infusion device 110 so as to deliver medication such as insulin to the patient. Moreover, in one embodiment, the cannula 170 is configured to be replaced with the replacement of the sensor 160.

In one aspect of the present invention, the cannula 170 and the sensor 160 may be configured to be subcutaneously positioned under the skin of the patient using an insertion mechanism (not shown) such as an insertion gun which may include, for example, a spring biased or loaded insertion mechanism to substantially accurately position the cannula 170 and the sensor 160 under the patient's skin. In this manner, the cannula 170 and the sensor 160 may be subcutaneously positioned with substantially little or no perceived pain by the patient. Alternatively, the cannula 170 and/or the sensor 160 may be configured to be manually inserted by the patient through the patient's skin. After positioning the cannula 170 and the sensor 160, they may be substantially firmly retained in position by an adhesive layer 180 which is configured to adhere to the skin of the patient for the duration of the time period during which the sensor 160 and the cannula 170 are subcutaneously positioned.

Moreover, in one embodiment, the transmitter unit 150 may be mounted after the subcutaneous positioning of the sensor 160 and the cannula 170 so as to be in electrical contact with the sensor electrodes. Similarly, the infusion tubing 130 may be configured to operatively couple to the housing of the transmitter unit 150 so as to be accurately positioned for alignment with the cannula 170 and to provide a substantially water tight seal. Additional detailed description of the analyte monitoring system including the sensor 160, transmitter unit 150 and the analyte monitor unit 120 is provided in U.S. Pat. No. 6,175,752, assigned to the assignee of the present invention, Abbott Diabetes Care Inc.

Referring back to FIG. 1, the infusion device 110 may include capabilities to program basal profiles, calculation of bolus doses including, but not limited to, correction bolus, carbohydrate bolus, extended bolus, and dual bolus, which may be performed by the patient using the infusion device 110, and may be based on one or more factors including the patient's insulin sensitivity, insulin on board, intended carbohydrate intake (for example, for the carbohydrate bolus calculation prior to a meal), the patient's measured or detected glucose level, and the patient's glucose trend information. In a further embodiment, the bolus calculation capabilities may also be provided in the analyte monitor unit 120.

In one embodiment, the analyte monitor unit 120 is configured with a substantially compact housing that can be easily carried by the patient. In addition, the infusion device 110 similarly may be configured as a substantially compact device which can be easily and conveniently worn on the patient's clothing (for example, housed in a holster or a carrying device worn or clipped to the patient's belt or other parts of the clothing). Referring yet again to FIG. 1, the analyte monitor unit 120 and/or the infusion device 110 may include a user interface such as information input mechanism by the patient as well as data output including, for example, the display unit 121 on the analyte monitor unit 120, or similarly a display unit 111 on the infusion device 110.

One or more audio output devices such as, for example, speakers or buzzers may be integrated with the housing of the infusion device 110 and/or the analyte monitor unit 120 so as to output audible alerts or alarms based on the occurrence of one or more predetermined conditions associated with the infusion device 110 or the analyte monitor unit 120. For example, the infusion device 110 may be configured to output an audible alarm or alert to the patient upon detection of an occlusion in the infusion tubing 130 or the occurrence of a timed event such as a reminder to prime the infusion tubing 130 upon replacement of the cannula 170, and the like. The analyte monitor unit 120 may similarly be configured to output an audible alarm or alert when a predetermined condition or a pre-programmed event occurs, such as, for example, a reminder to replace the sensor 160 after its useful life (of 3 days, 5 days or 7 days), or one or more alerts associated with the data received from the transmitter unit 150 corresponding to the patient's monitored analyte levels. Such alerts or alarms may include a warning alert to the patient that the detected analyte level is beyond a predetermined threshold level, or the trend of the detected analyte levels within a given time period is indicative of a significant condition such as potential hyperglycemia or hypoglycemia, which require attention or corrective action. It is to be noted that the examples of audible alarms and/or alerts are described above for illustrative purposes only, that within the scope of the present invention, other events or conditions may be programmed into the infusion device 110 or the analyte monitor unit 120 or both, so as to alert or notify the patient of the occurrence or the potential occurrence of such events or conditions.

In addition, within the scope of the present invention, audible alarms may be output alone, or in combination with one or more of a visual alert such as an output display on the display unit 111, 121 of the infusion device 110 or the analyte monitor unit 120, respectively, or vibratory alert which would provide a tactile indication to the patient of the associated alarm and/or alert.

Moreover, referring yet again to FIG. 1, while one analyte monitor unit 120 and one transmitter unit 150 are shown, within the scope of the present invention, additional analyte monitor units or transmitter units may be provided such that, for example, the transmitter unit 150 may be configured to transmit to multiple analyte monitor units substantially simultaneously. Alternatively, multiple transmitter units coupled to multiple sensors concurrently in fluid contact with the patient's analyte may be configured to transmit to the analyte monitor unit 120, or to multiple analyte monitor units. For example, an additional transmitter unit coupled to an additional sensor may be provided in the integrated infusion device 110 and analyte monitoring system 100 which does not include the cannula 170, and which may be used to perform functions associated with the sensor 160 such as sensor calibration, sensor data verification, and the like.

In one embodiment, the transmitter unit 150 is configured to transmit the sampled data signals received from the sensor 160 without acknowledgement from the analyte monitor unit 120 that the transmitted sampled data signals have been received. For example, the transmitter unit 150 may be configured to transmit the encoded sampled data signals at a fixed rate (e.g., at one minute intervals) after the completion of the initial power on procedure. Likewise, the analyte monitor unit 120 may be configured to detect such transmitted encoded sampled data signals at predetermined time intervals. Alternatively, the transmitter unit 150 and the analyte monitor unit 120 may be configured for bi-directional communication over the communication path 140.

Additionally, in one aspect, the analyte monitor unit 120 may include two sections. The first section of the analyte monitor unit 120 may include an analog interface section that is configured to communicate with the transmitter unit 150 via the communication path 140. In one embodiment, the analog interface section may include a radio frequency (RF) receiver and an antenna for receiving and amplifying the data signals from the transmitter unit 150, which are thereafter, demodulated with a local oscillator and filtered through a band-pass filter. The second section of the analyte monitor unit 120 may include a data processing section which is configured to process the data signals received from the transmitter unit 150 such as by performing data decoding, error detection and correction, data clock generation, and data bit recovery, for example.

In operation, upon completing the power-on procedure, the analyte monitor unit 120 is configured to detect the presence of the transmitter unit 150 within its range based on, for example, the strength of the detected data signals received from the transmitter unit 150 or a predetermined transmitter identification information. Upon successful synchronization with the transmitter unit 150, the analyte monitor unit 120 is configured to begin receiving from the transmitter unit 150 data signals corresponding to the patient's detected analyte, for example glucose, levels.

Referring again to FIG. 1, the analyte monitor unit 120 or the infusion device 110, or both may be configured to further communicate with a data processing terminal (not shown) which may include a desktop computer terminal, a data communication enabled kiosk, a laptop computer, a handheld computing device such as a personal digital assistant (PDAs), or a data communication enabled mobile telephone, and the like, each of which may be configured for data communication via a wired or a wireless connection. The data processing terminal for example may include physician's terminal and/or a bedside terminal in a hospital environment, for example.

The communication path 140 for data communication between the transmitter unit 150 and the analyte monitor unit 120 of FIG. 1 may include an RF communication link, Bluetooth communication link, infrared communication link, or any other type of suitable wireless communication connection between two or more electronic devices. The data communication link may also include a wired cable connection such as, for example, but not limited to an RS232 connection, USB connection, or serial cable connection.

Referring yet again to FIG. 1, in a further aspect of the present invention, the analyte monitor unit 120 or the infusion device 110 (or both) may also include a test strip port configured to receive a blood glucose test strip for discrete sampling of the patient's blood for glucose level determination. An example of the functionality of the blood glucose test strip meter unit may be found in the Freestyle® Blood Glucose Meter available from the assignee of the present invention, Abbott Diabetes Care Inc.

In the manner described above, in one embodiment of the present invention, the cannula 170 for infusing insulin or other suitable medication is integrated with the adhesive patch 180 for the sensor 160 and the transmitter unit 150 of the analyte monitoring system. Accordingly, only one on-skin patch can be worn by the patient (for example, on the skin of the abdomen) rather than two separate patches for the infusion device cannula 170, and the analyte monitoring system sensor 160 (with the transmitter unit 150). Thus, the Type-1 diabetic patient may conveniently implement infusion therapy in conjunction with real time glucose monitoring while minimizing potential skin irritation on the adhesive patch 180 site on the patient's skin, and thus provide more insertion sites with less irritation.

In addition, the integrated infusion device and analyte monitoring system 100 as shown in FIG. 1 may be configured such that the infusion tubing 130 may be disconnected from the infusion device 110 as well as from the housing of the transmitter 150 (or the adhesive patch 180) such that, optionally, the patient may configure the system as a continuous analyte monitoring system while disabling the infusion device 110 functionality.

Moreover, in accordance with one embodiment of the present invention, the patient may better manage the physiological conditions associated with diabetes by having substantially continuous real time glucose data, trend information based on the substantially continuous real time glucose data, and accordingly, modify or adjust the infusion levels delivered by the infusion device 110 from the pre-programmed basal profiles that the infusion device 110 is configured to implement.

Figure 2:
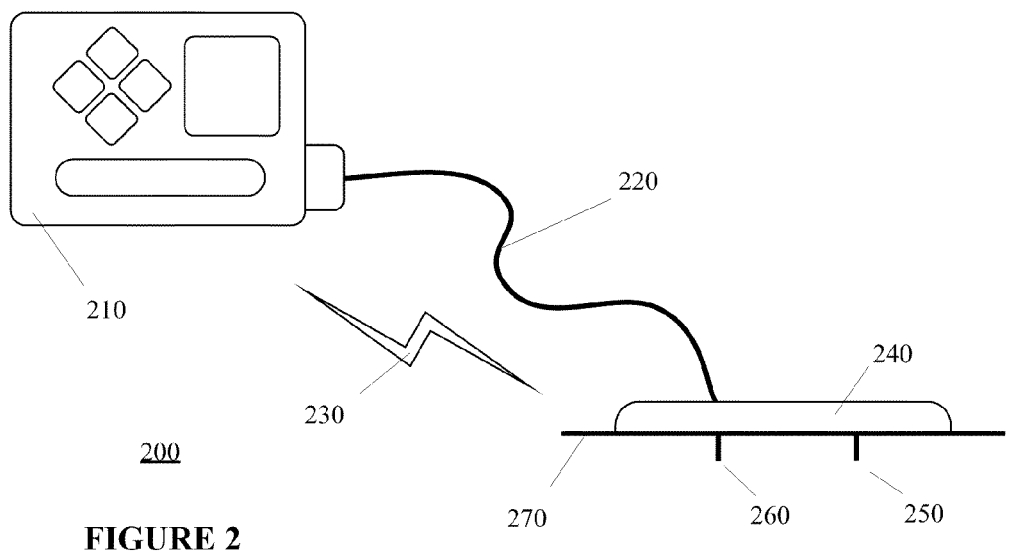
FIG. 2 illustrates an integrated infusion device and analyte monitoring system in accordance with another embodiment of the present invention.

FIG. 2 illustrates an integrated infusion device and analyte monitoring system in accordance with another embodiment of the present invention. Referring to FIG. 2, the integrated infusion device and analyte monitoring system 200 in one embodiment of the present invention includes an integrated infusion device and analyte monitor unit 210 which is coupled to an infusion tubing 220 connected to the cannula 260. Also shown in FIG. 2 is a transmitter unit 240 which is in electrical contact with an analyte sensor 250, where the cannula 260 and the analyte sensor 250 are subcutaneously positioned under the skin of the patient, and retained in position by an adhesive layer or patch 270.

Referring to FIG. 2, the integrated infusion device 200 and analyte monitor unit 210 is configured to wirelessly communicate with the transmitter unit 240 over a communication path 230 such as an RF communication link. Compared with the embodiment shown in FIG. 1, it can be seen that in the embodiment shown in FIG. 2, the infusion device and the analyte monitor are integrated into a single housing 210. In this manner, the transmitter unit 240 may be configured to transmit signals corresponding to the detected analyte levels received from the analyte sensor 250 to the integrated infusion device and 200 analyte monitor unit 210 for data analysis and processing.

Accordingly, the patient may conveniently receive real time glucose levels from the transmitter unit 240 and accordingly, determine whether to modify the existing basal profile(s) in accordance with which insulin is delivered to the patient. In this manner, the functionalities of the analyte monitor unit may be integrated within the compact housing of the infusion device to provide additional convenience to the patient by, for example, providing the real time glucose data as well as other relevant information such as glucose trend data to the user interface of the infusion device, so that the patient may readily and easily determine any suitable modification to the infusion rate of the insulin pump.

In one embodiment, the configurations of each component shown in FIG. 2 including the cannula 260, the analyte sensor 250, the transmitter unit 240, the adhesive layer 270, the communication path 230, as well as the infusion tubing 220 and the functionalities of the infusion device and the analyte monitor are substantially similar to the corresponding respective component as described above in conjunction with FIG. 1.

Accordingly, in one embodiment of the present invention, the additional convenience may be provided to the patient in maintaining and enhancing diabetes management by, for example, having a single integrated device such as the integrated infusion device and analyte monitor unit 210 which would allow the patient to easily manipulate and manage insulin therapy using a single user interface system of the integrated infusion device and analyte monitor unit 210. Indeed, by providing many of the information associated with the glucose levels and insulin infusion information in one device, the patient may be provided with the additional convenience in managing diabetes and improving insulin therapy.

Figure 3:
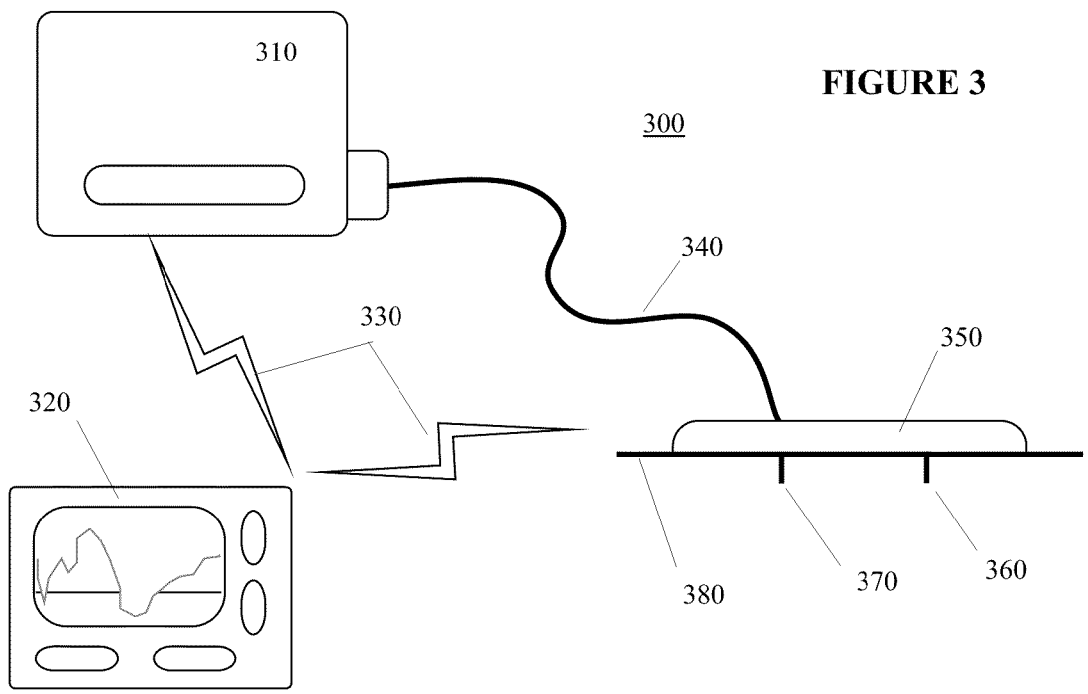
FIG. 3 illustrates an integrated infusion device and analyte monitoring system in accordance with yet another embodiment of the present invention.

FIG. 3 illustrates an integrated infusion device and analyte monitoring system in accordance with yet another embodiment of the present invention. Referring to FIG. 3, the integrated infusion device and analyte monitoring system 300 in one embodiment of the present invention includes an infusion device 310 connected to an infusion tubing 340 coupled to a cannula 370. The cannula 370 is configured to be positioned subcutaneously under the patient's skin and substantially retained in position by an adhesive layer 380. Also retained in position, as discussed above and similar to the embodiments described in conjunction with FIGS. 1-2, is an analyte sensor 360 also positioned subcutaneously under the patient's skin and maintained in fluid contact with the patient's analyte. A transmitter unit 350 is provided so as to be electrically coupled to the analyte sensor 360 electrodes. Also, as can be seen from FIG. 3, in one embodiment, the infusion tubing 340 is connected to the housing of the transmitter unit 350 so as to connect to the cannula 370 disposed under the patient's skin.

Referring to FIG. 3, also provided is an analyte monitor unit 320 configured to wirelessly communicate with the transmitter unit 350 to receive data therefrom associated with the analyte levels of the patient detected by the analyte sensor 360. Referring to FIG. 3, in one embodiment, the infusion device 310 does not include a user interface such as a display unit and/or an input unit such as buttons or a jog dial. Instead, the user interface and control mechanism is provided on the analyte monitoring unit 320 such that the analyte monitoring unit 320 is configured to wirelessly control the operation of the infusion device 310 and further, to suitably program the infusion device 310 to execute pre-programmed basal profile(s), and to otherwise control the functionality of the infusion device 310.

More specifically, all of the programming and control mechanisms for the infusion device 310 are provided in the analyte monitoring unit 320 such that when the patient is wearing the infusion device 310, it may be worn discreetly under clothing near the infusion site on the patient's skin (such as abdomen), while still providing convenient access to the patient for controlling the infusion device 310 through the analyte monitoring unit 320.

In addition, in one embodiment, the configurations of each component shown in FIG. 3 including the cannula 370, the analyte sensor 360, the transmitter unit 350, the adhesive layer 380, the communication path 330, as well as the infusion tubing 340 and the functionalities of the infusion device and the analyte monitoring unit 320 are substantially similar to the corresponding respective component as described above in conjunction with FIG. 1. However, the infusion device 310 in the embodiment shown in FIG. 3 is configured with a transceiver or an equivalent communication mechanism to communicate with the analyte monitoring unit 320.

In this manner, in one embodiment of the present invention, configuration of the infusion device 310 without a user interface provides a smaller and lighter housing and configuration for the infusion device 310 which would enhance the comfort in wearing and/or carrying the infusion device 310 with the patient. Moreover, since the control and programming functions of the infusion device 310 are provided on the analyte monitoring unit 320, the patient may conveniently program and/or control the functions and operations of the infusion device 310 without being tethered to the infusion tubing 340 attached to the cannula 370 which is positioned under the patient's skin. In addition, since the programming and control of the infusion device 310 is remotely performed on the analyte monitoring unit 320, the infusion tubing 340 may be shorter and thus less cumbersome.

Figure 4:
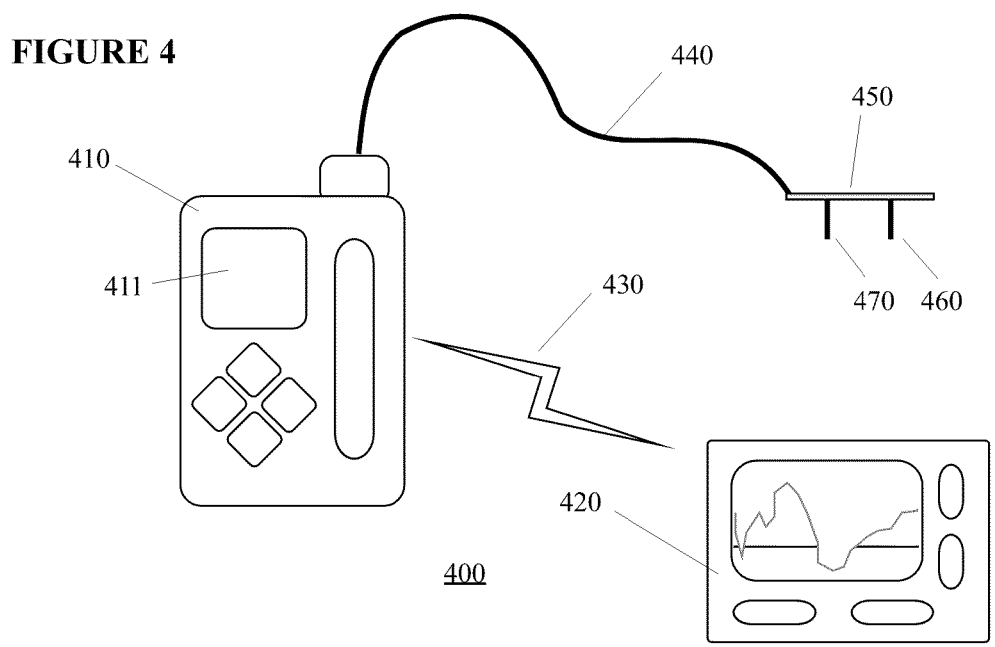
FIG. 4 illustrates an integrated infusion device and analyte monitoring system in accordance with still another embodiment of the present invention.

FIG. 4 illustrates an integrated infusion device and analyte monitoring system in accordance with still another embodiment of the present invention. Referring to FIG. 4, the integrated infusion device and analyte monitoring system 400 in one embodiment of the present invention includes an infusion device 410 configured to wirelessly communicate with an analyte monitoring unit 420 over a communication path 430 such as an RF (radio frequency) link. In addition, as can be further seen from FIG. 4, the infusion device 410 is connected to an infusion tubing 440 which has provided therein integral wires connected to the analyte sensor electrodes. As discussed in further detail below, the measured analyte levels of the patient is received by the infusion device 410 via the infusion tubing 440 and transmitted to the analyte monitoring unit 420 for further processing and analysis.

More specifically, referring to FIG. 4, the integrated infusion device and analyte monitoring system 400 includes a patch 450 provided with a cannula 470 and an analyte sensor 460. The cannula 470 is configured to deliver or infuse medication such as insulin from the infusion device 410 to the patient. That is, in one embodiment, the cannula 470 and the analyte sensor 460 are configured to be positioned subcutaneous to the patient's skin. The analyte sensor 460 is configured to be positioned to be in fluid contact with the patient's analyte.

In this manner, the analyte sensor 460 is electrically coupled to integral wires provided within the infusion tubing 440 so as to provide signals corresponding to the measured or detected analyte levels of the patient to the infusion device 410. In one embodiment, the infusion device 410 is configured to perform data analysis and storage, such that the infusion device 410 may be configured to display the real time measured glucose levels to the patient on its display unit 411. In addition to, or alternatively, the infusion device 410 is configured to wirelessly transmit the received signals from the analyte sensor 460 to the analyte monitoring unit 420 for data analysis, display, and/or storage and the analyte monitoring unit 420 may be configured to remotely control the functions and features of the infusion device 410, providing additional user convenience and discreteness.

Referring back to FIG. 4, in one embodiment, the patch 450 may be configured to be substantially small without a transmitter unit mounted thereon, and provided with a relatively small surface area to be attached to the patient's skin. In this manner, the patient may be provided with added comfort in having a substantially compact housing mounted on the skin (attached with an adhesive layer, for example), to infuse medication such as insulin, and for continuous analyte monitoring with the analyte sensor 460.

Figure 5:
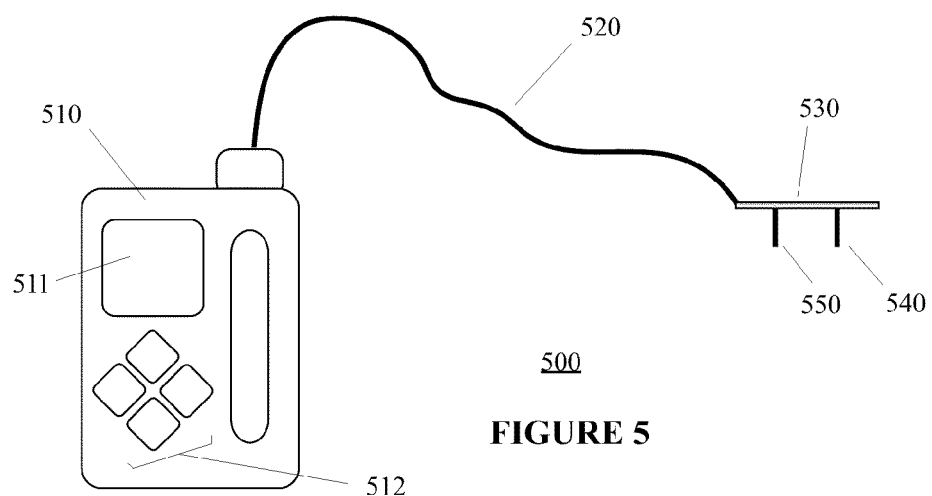
FIG. 5 illustrates an integrated infusion device and analyte monitoring system in accordance with still a further embodiment of the present invention.

FIG. 5 illustrates an integrated infusion device and analyte monitoring system in accordance with still a further embodiment of the present invention. As compared with the embodiment shown in FIG. 4, the integrated infusion device and analyte monitoring system 500 of FIG. 5 includes an integrated infusion device and analyte monitoring unit 510. Accordingly, one user interface is provided to the user including the display unit 511 and input buttons 512 provided on the housing of the integrated infusion device and analyte monitoring unit 510. Also shown in FIG. 5 is infusion tubing 520 with integral wires disposed therein and connected to an analyte sensor 540 electrodes in fluid contact with the patient's analyte. Moreover, as can be seen from FIG. 5, an adhesive patch 530 is provided to retain the subcutaneous position of a cannula 550 and the analyte sensor 540 in the desired positions under the patient's skin.

Optionally, the integrated infusion device and analyte monitoring unit 510 may be provided with wireless or wired communication capability so to communicate with a remote terminal such as a physician's computer terminal over a wireless communication path such as RF communication link, or over a cable connection such as a USB connection, for example. Referring back to FIG. 5, in one embodiment of the present invention, the diabetic patient using an infusion therapy is provided with less components to handle or manipulate further simplifying insulin therapy and glucose level monitoring and management.

Figure 6:
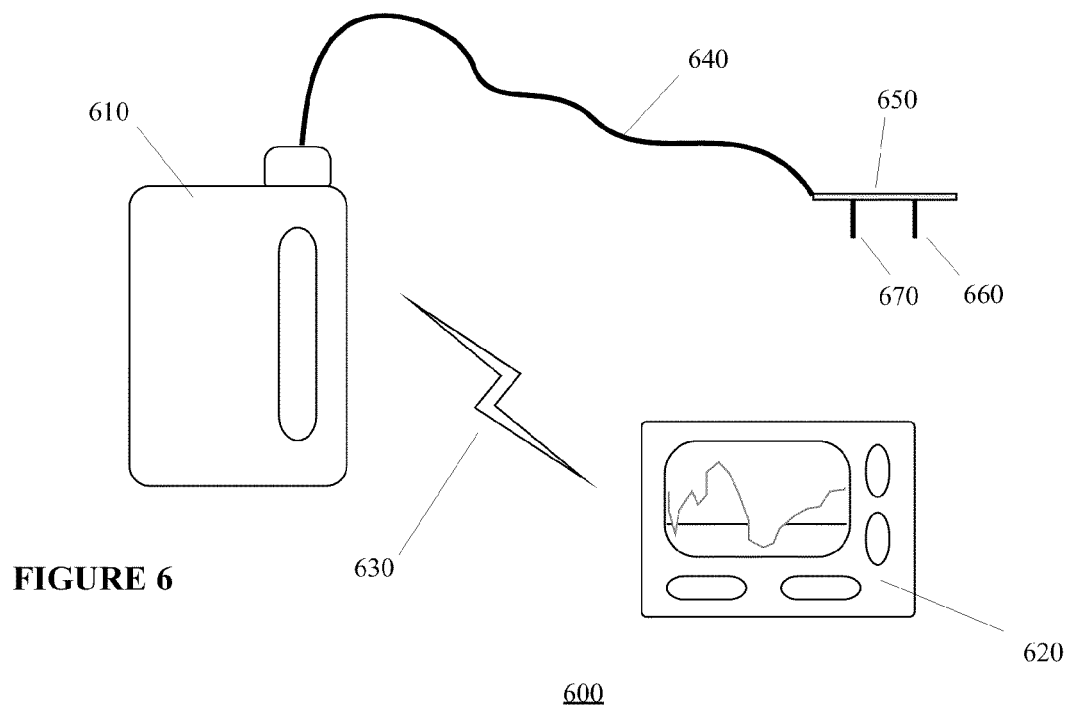
FIG. 6 illustrates an integrated infusion device and monitoring system in accordance with yet still a further embodiment of the present invention.

FIG. 6 illustrates an integrated infusion device and monitoring system in accordance with yet still a further embodiment of the present invention. Referring to FIG. 6, the integrated infusion device and analyte monitoring system 600 is provided with an infusion device without a user interface, and configured to wirelessly communicate with an analyte monitoring unit 620 over a communication path 630 such as an RF link. The infusion device 610 which may be provided in a compact housing since it does not incorporate the components associated with a user interface, is connected to an infusion tubing 640 having disposed therein integral wires correspondingly connected to the electrodes of analyte sensor 660 in fluid contact with the patient's analyte. In addition, the compact adhesive patch 650 in one embodiment is configured to retain cannula 670 and the analyte sensor 660 in the desired position under the skin of the patient.

Similar to the embodiment shown in FIG. 3, the analyte monitoring unit 620 is configured to control and program the infusion device 610 over the communication link 630. In this manner, the control and programming functions of the infusion device 610 may be remotely performed by the analyte monitoring unit 620, providing convenience to the patient.

Figure 7A:
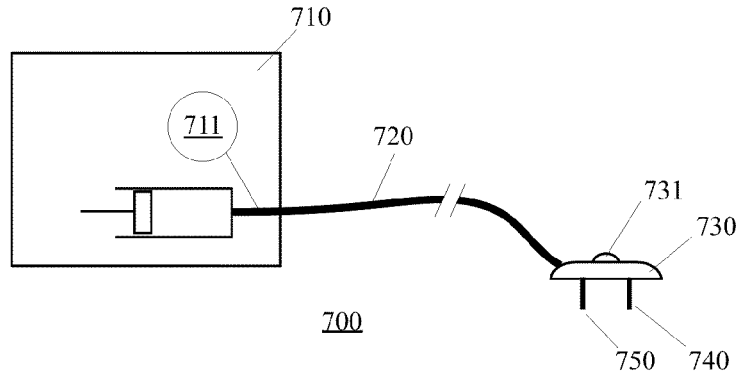
Figure 7B:
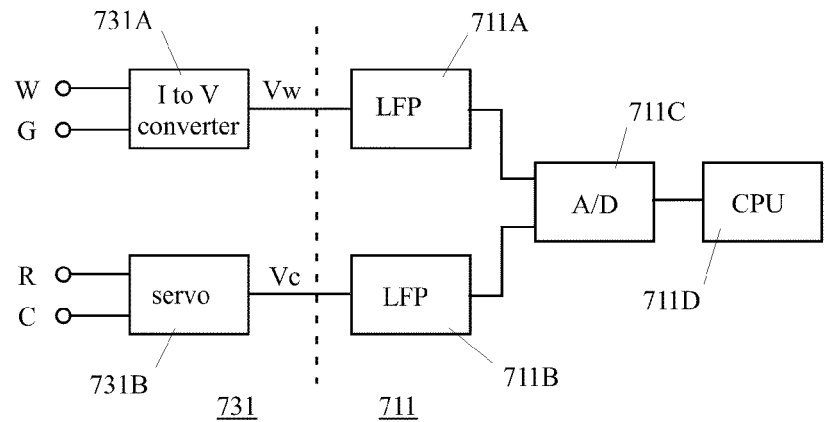
FIGS. 7B-7C illustrate the analog front end circuitry located at the patient interface and the pump assembly, respectively, of the integrated infusion device and monitoring system shown in FIG. 7A in accordance with one embodiment of the present invention.
Figure 7C:
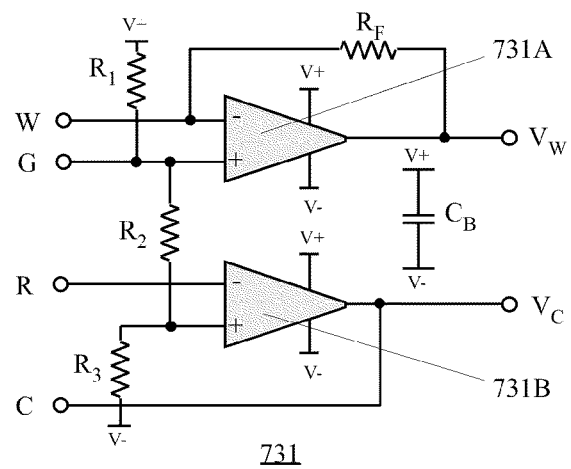

FIG. 7A illustrates the integrated infusion device and monitoring system shown in FIG. 6 in further detail in one embodiment of the present invention, while FIGS. 7B-7C illustrate the analog front end circuitry located at the patient interface and the pump assembly, respectively, of the integrated infusion device and monitoring system shown in FIG. 7A in accordance with one embodiment of the present invention. Referring to FIG. 7A, an infusion device 710 connected to an infusion tubing 720 with integral wires provided therein for connection to the electrodes of the analyte sensor is shown. The infusion tubing 720 is further connected to an adhesive patch 730 which is configured to retain cannula 750 and analyte sensor 740 in the desired subcutaneous position under the skin of the patient.

Referring to FIG. 7A, in one embodiment of the present invention, the infusion device 710 may be provided with a first analog front end circuitry unit 711, while the adhesive patch may be provided with a second analog front end circuitry unit 731. The integral wires from the analyte sensor 740 is configured to extend from the infusion device 710 to the adhesive layer 730 via the infusion tubing 720. Since the analyte sensor 740 in one embodiment is a passive component, the signals on the working electrode and the reference electrodes of the analyte sensors are subject to noise given the high impedance of the electrodes and the length of the integral wires (in excess of a few centimeters). The noise in turn may potentially adversely affect the signals on the working and reference electrodes which may distort the measured analyte levels detected by the analyte sensor 740.

Given the length of the integral wire which corresponds to the length of the infusion tubing 720, in one embodiment, the signals from the working and reference electrodes may be converted to low impedance signals to minimize adverse impact from the noise. Accordingly, the infusion device 710 may be provided with a first analog front end circuitry unit 711, while the adhesive patch 730 may be provided with a second analog front end circuitry unit 731 as discussed in further detail below in conjunction with FIGS. 7B and 7C.

Referring now to FIG. 7B, the second analog front circuitry unit 731 disposed on the adhesive patch 730 on the patient's skin, in one embodiment includes a trans-impedance amplifier (current to voltage converter or "I-to-V") 731A configured to convert the working electrode (W) current to a voltage (Vw), and to provide a guard signal (G), and a servo segment 731B to drive the counter electrode (C) voltage (Vc) based on the reference electrode (R) voltage. Also shown in FIG. 7B is a Low-Pass Filter (LPF) and gain stage 711A that follow each of the I-to-V and servo stages, and which is configured in one embodiment to drive an A/D (Analog-to-Digital) converter unit 711C whose results are read by a controller such as a central processing unit (CPU) 711D. The A/D converter unit 711C and the CPU 711D and other peripherals may be combined into a single integrated circuit (IC) known as a microcontroller (μC) such as the MSP430 product line.

Referring now to FIG. 7C, in one embodiment, the second analog front end circuitry unit 731 may be implemented by a pair of operational amplifiers (731A and 731B), four resistors (R1, R2, R3, Rf), and a bypass capacitor (Cb). The I-to-F stage using operational amplifier 731A is generated by the action of the input current from the working electrode (W) flowing through the feedback resistor (Rf) and creating a voltage differential that is driven by the operational amplifier 731A as the low impedance signal Vw. The offset for the Vw signal is established by the resistor divider comprised of R1, R2 and R3 which also creates the voltage of the guard signal (G)—a signal that is at the same potential or voltage as the working electrode (W).

The servo, using operational amplifier 731B, in one embodiment, drives the counter electrode (C) voltage to the sensor so that the reference electrode (R) is at the second value set by the resistor divider comprised of resistors R1, R2 and R3. This maintains the working electrode (W) voltage above the reference electrode (R) by a set amount known as the "Poise Voltage" (i.e. 40 mV). The bypass capacitor (Cb) may be a small, low equivalent series resistance (ESR) capacitor, such as a 0.1 uF (100 nF) multi-layer ceramic (MLC) capacitor, that acts to provide local energy and reduce noise on the circuit. The voltage source for this circuit may be provided by the potential difference between V+ and V− where, for example, V+ may be 5V and V− may be ground (GND) or V+ may be +3V and V− may be −3V.

In one embodiment, the operational amplifiers 731A, 731B may be acquired as a dual operational amplifier integrated circuit (IC) in a single, small 8-pin, surface mount technology (SMT) package such as the OPA2349 in a SOT23-8 package (3 mm by 3 mm). Similar dual operational amplifier products may be available in even smaller ball-grid array (BGA) packages and as bare die that may be mounted directly to the circuit substrate, such as a printed circuit board (PCB) or flex circuit, using techniques such as "flip-chip" and wire-bond.

Figure 8A:
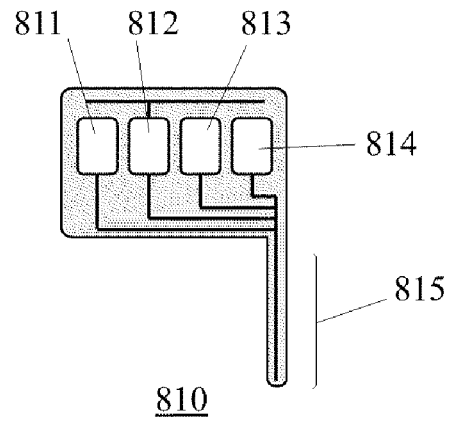
FIGS. 8A-8C illustrate a passive sensor configuration for use in a continuous analyte monitoring system, and two embodiments of an active sensor configuration for use at the patient interface in the integrated infusion device and monitoring system, respectively, in accordance with one embodiment of the present invention.
Figure 8C:
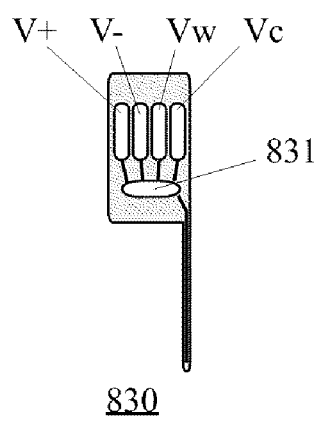
Figure 8B:
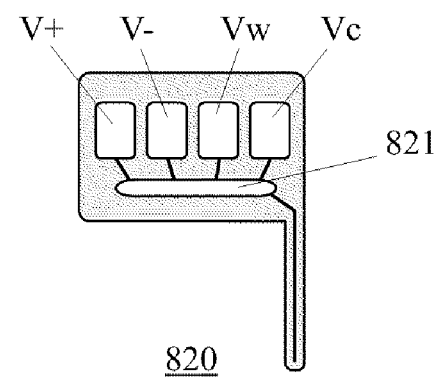

FIGS. 8A-8C illustrate a passive sensor configuration for use in a continuous analyte monitoring system, and two embodiments of an active sensor configuration for use at the patient interface in the integrated infusion device and monitoring system, respectively, in accordance with one embodiment of the present invention. Referring to FIG. 8A, analyte sensor 810 includes working electrode 811, a guard trace 812, a reference electrode 813, and a counter electrode 814. In one embodiment, the "tail" segment 815 of the analyte sensor 810 is configured to be positioned subcutaneously under the patient's skin so as to be in fluid contact with the patient.

Referring now to FIG. 8B, analyte sensor 820 is provided with the analog front end portion 821 where the four contacts shown are V+, V−, Vw, and Vc signals in accordance with one embodiment in place of the working electrode 811, a guard trace 812, a reference electrode 813, and a counter electrode 814, respectively. In this manner, in one embodiment of the present invention, these signals of the active analyte sensor 820 are low impedance and thus less subject to noise than the passive sensor signals. Moreover, in one embodiment, the analyte sensor 820 configuration may include a flex circuit.

Referring now to FIG. 8C, in a further embodiment, an active sensor of similar construction to the active sensor 820 of FIG. 8B but with much smaller dimensions is shown. More specifically, analyte sensor 830 is provided with four contacts configured for direct wire bonding rather than a mechanical contact system as indicated by the large contact areas on the previous two sensor configurations shown in FIGS. 8A-8B. Since the shape of the analyte sensor 830 is reduced, the sensor 830 may be wrapped around the cannula (for example, cannula 470 of FIG. 4) and thus only a single entry site may be required for the patient analyte monitoring and insulin infusion. Moreover, within the scope of the present invention, additional sensor/cannula configurations may be provided where the sensor circuitry and cannula are created as a single assembly such as a cannula with the circuit 831 fabricated on the surface.

Figure 9:
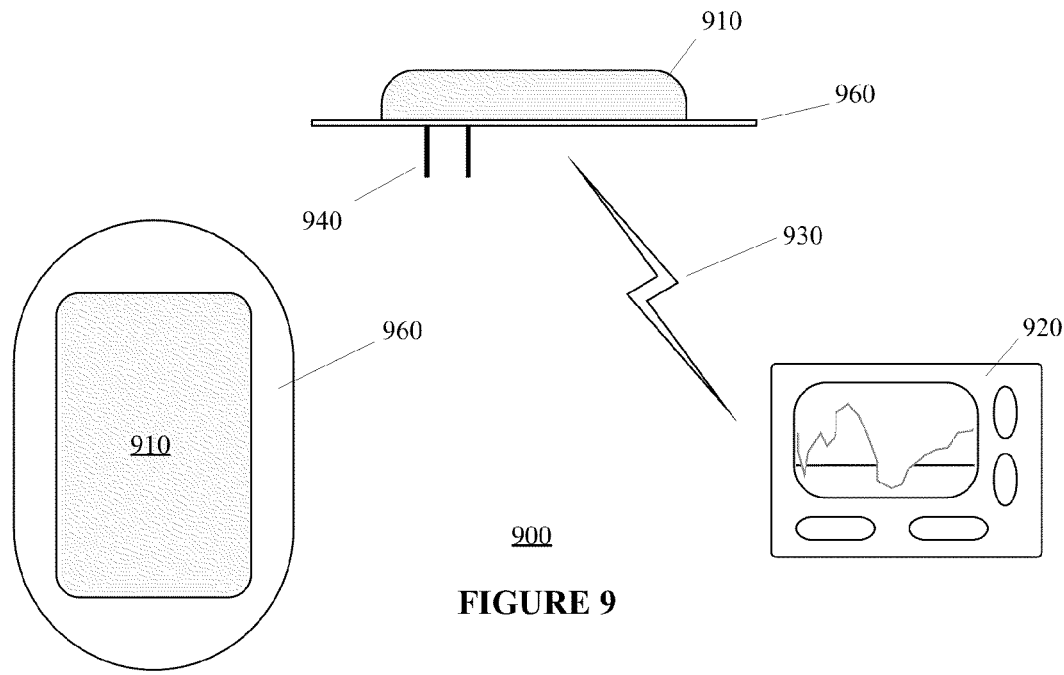
FIG. 9 illustrates an integrated infusion device and analyte monitoring system with the infusion device and the monitoring system transmitter integrated into a single patch worn by the patient in accordance with one embodiment of the present invention.

FIG. 9 illustrates an integrated infusion device and analyte monitoring system with the infusion device and the monitoring system transmitter integrated into a single patch worn by the patient in accordance with one embodiment of the present invention. Referring to FIG. 9, the integrated infusion device and analyte monitoring system 900 includes an integrated patch pump and transmitter unit 910 provided on an adhesive layer 960, which is configured to be placed on the skin of the patient, so as to securely position cannula 950 and analyte sensor 940 subcutaneously under the skin of the patient. The housing of the integrated infusion pump and transmitter unit 910 is configured in one embodiment to include the infusion mechanism to deliver medication such as insulin to the patient via the cannula 950.

In addition, the integrated patch pump and transmitter unit 910 is configured to transmit signals associated with the detected analyte levels measured by the analyte sensor 940, over a wireless communication path 930 such as an RF link. The signals are transmitted from the on body integrated patch pump and transmitter unit 910 to a controller unit 920 which is configured to control the operation of the integrated patch pump and transmitter unit 910, as well as to receive the transmitted signals from the integrated patch pump and transmitter unit 910 which correspond to the detected analyte levels of the patient.

Referring back to FIG. 9, in one embodiment, the infusion mechanism of the integrated patch pump and transmitter unit 910 may include the infusion device of the type described in U.S. Pat. No. 6,916,159 assigned to the assignee of the present invention Abbott Diabetes Care Inc. In addition, while a wireless communication over the communication path 930 is shown in FIG. 9, the wireless communication path 930 may be replaced by a set of wires to provide a wired connection to the controller unit 920.

In this manner, in one embodiment of the present invention, the integrated infusion device and analyte monitoring system 900 does not use an infusion tubing which may provide additional comfort and convenience to the patient by providing additional freedom from having to wear a cumbersome tubing.

Figure 10:
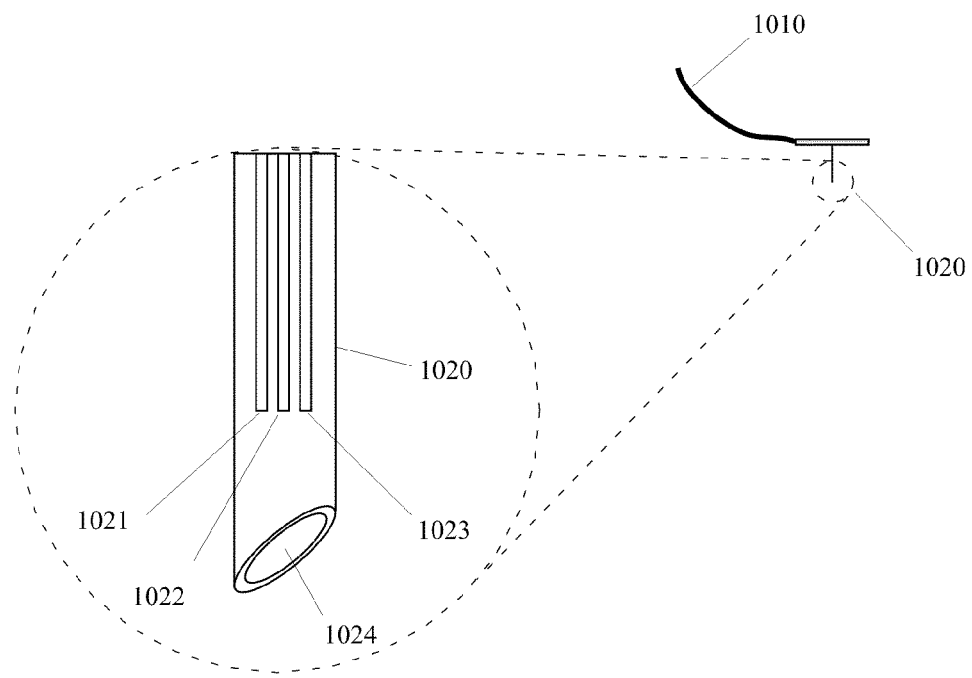
FIG. 10 is a detailed view of the infusion device cannula integrated with analyte monitoring system sensor electrodes in accordance with one embodiment of the present invention.

FIG. 10 is a detailed view of the infusion device cannula integrated with analyte monitoring system sensor electrodes in accordance with one embodiment of the present invention. Referring to FIG. 10, there is shown an infusion device cannula with analyte sensor electrodes 1020 disposed therein, and mounted to an adhesive patch 1010 so as to retain its position securely in the patient. More specifically, as can be seen from FIG. 10, the cannula with analyte sensor electrodes 1020 include sensor electrodes 1021, 1022, 1023 (which may correspond to working, reference and counter electrodes, respectively) each of which are provided within the cannula tip 1020, and further, positioned so as to maintain fluid contact with the patient's analyte.

Figure 12A:
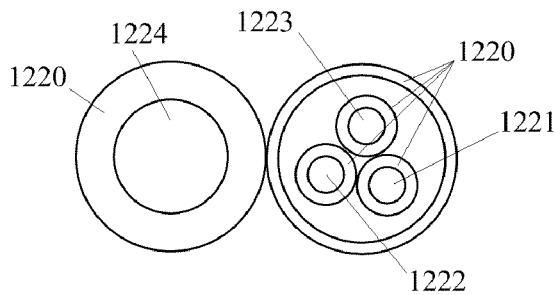
FIGS. 12A-12C each illustrate a cross sectional view of the infusion device cannula integrated with continuous analyte monitoring system sensor electrodes of FIG. 10 in accordance with the various embodiments respectively, of the present invention.
Figure 12B:
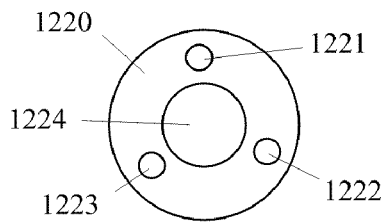
Figure 12C:
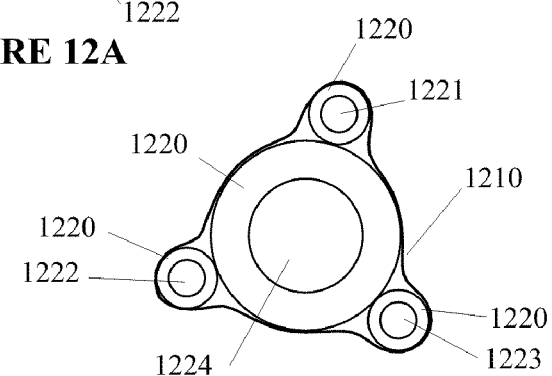

FIGS. 12A-12C each illustrate a cross sectional view of the infusion device cannula integrated with continuous analyte monitoring system sensor electrodes of FIG. 10 in accordance with the various embodiments respectively, of the present invention. Referring to FIG. 12A, in one embodiment, the wire and tubing are provided in parallel such that the tubing wall 1220, the tube bore for insulin flow 1224, the wire outer casing 1220 and the individual insulated wires 1221, 1222, 1223 are substantially provided as shown in FIG. 12A. More specifically, it can be seen from the Figure that each of the three insulated wires are provided with an insulation layer 1020 of tubing wall individually surrounding each insulated wires 1221, 1222, 1223, and further, where the three insulated wires 1221, 1222, 1223 are in turn surrounded by the tubing wall 1220.

Referring now to FIG. 12B in one embodiment of the present invention, the insulated wires 1221, 1222, 1223 respectively connected to the sensor electrodes are co-extruded into tubing wall 1220, with the tube bore 1224 for insulin delivery and the insulated wires 1221, 1222, 1223 configured substantially as shown in the FIG. 12B. Referring now to FIG. 12C, in still a further embodiment of the present invention, each of the insulated wires 1221, 1222, and 1223 are wrapped around the tubing 1220 and covered with a sheath 1210, thus providing the tubing wall 1220, the tubing bore 1224 for insulin delivery, the individual insulated wires 1221, 1222, 1223, and the outer protective sheath 1210, which may also serve as an electromagnetic shield to eliminate electronic noise as substantially shown in the Figure.

Referring again to the Figures, the embodiments shown in FIGS. 12A and 12C may have a larger cross-sectional area (thus a larger hole needed to be punctured on the skin of the patient), but are likely easier to manufacture, and more reliable and easier to make connection to the analyte sensor electronics). Additionally, within the scope of the present invention, an optical data transmission (i.e. fiber optics) along insulin delivery tubing between sensor and pump may be provided instead of integral wires as discussed above.

Figure 11A:
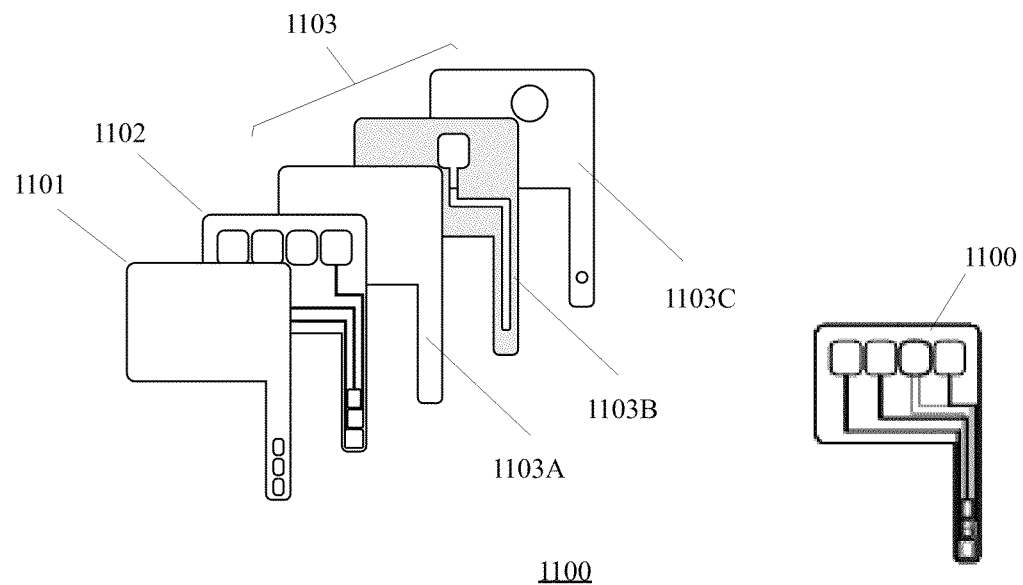
Figure 11B:
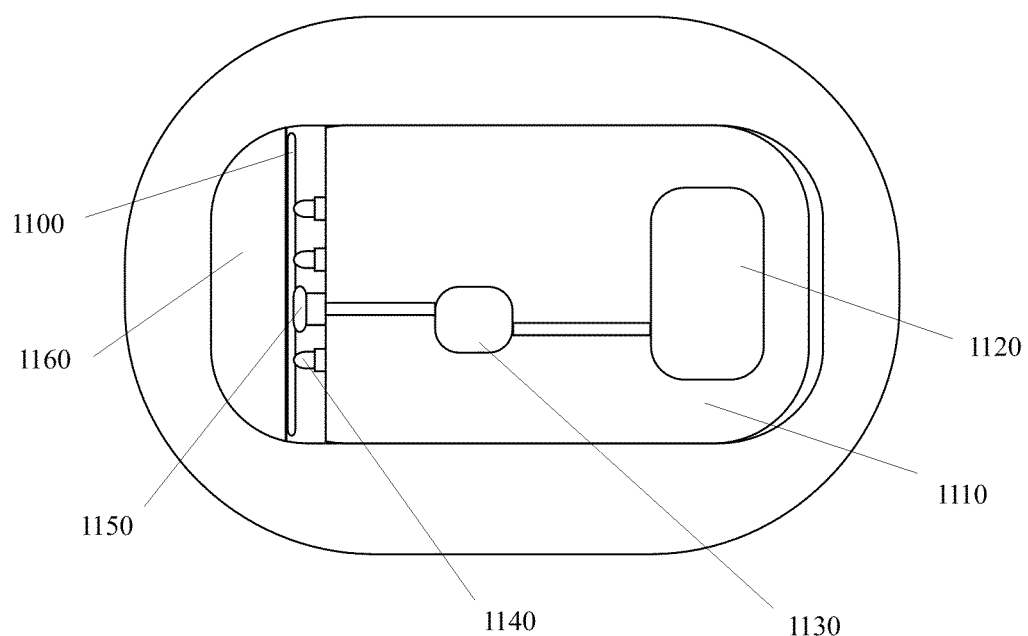
FIG. 11B illustrates a top planar view of the analyte monitoring system transmitter unit integrated with the infusion device in accordance with one embodiment of the present invention.

FIG. 11A illustrates a component perspective view of the infusion device cannula integrated with analyte monitoring system sensor electrodes in accordance with another embodiment of the present invention, while FIG. 11B illustrates a top planar view of the analyte monitoring system transmitter unit integrated with an infusion device in accordance with one embodiment of the present invention. Referring to FIGS. 11A-11B, in one embodiment of the present invention, integrated analyte sensor and infusion device cannula 1100 comprises five laminated layers including a top insulation layer 1101, a conductive layer 1102 with electrode traces disposed thereon, followed by three layer substrate with integrated infusion cannula 1103.

In one embodiment, the three layer substrate with integrated infusion cannula 1103 includes a separation/insulation layer 1103A to insulate the sensor electrodes from the infusion cannula, a channel layer 1103B configured to guide the flow of the insulin or any other suitable medication, and an inlet/outlet layer 1103C. Also shown in FIG. 11A is an assembled view of the integrated analyte sensor and infusion device cannula 1100.

Referring now to FIG. 11B, it can be seen that a patch pump as shown in one embodiment is provided with a transmitter unit 1110 and an insulin pump 1130 coupled to insulin reservoir 1120, and operatively coupled or mounted to the transmitter unit 1110. Also shown in FIG. 11B is the analyte sensor contacts 1140 which are configured to establish electrical contact with the respective electrodes of the integrated infusion cannula and analyte sensor 1100. Also shown in FIG. 11B is insulin port 1150 which is connected to the channel layer 1103B of the integrated infusion device cannula and analyte sensor 1100.

In this manner, in one embodiment of the present invention, the patch pump may be worn by the patient on skin and which includes the insulin infusion mechanism as well as the analyte sensor and transmitter unit.

Figure 13:
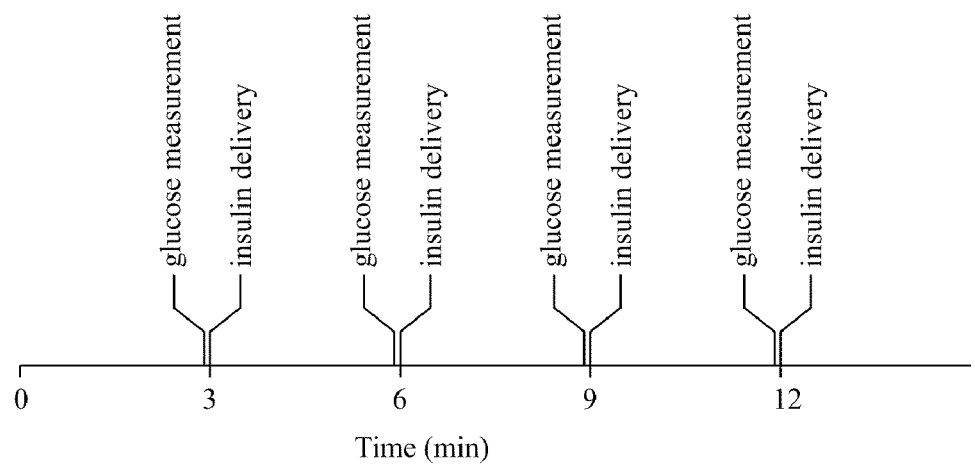
FIG. 13 is a timing chart for illustrating the temporal spacing of blood glucose measurement and insulin delivery by the integrated infusion device and monitoring system in one embodiment.

FIG. 13 is a timing chart for illustrating the temporal spacing of blood glucose measurement and insulin delivery by the integrated infusion device and monitoring system in one embodiment. More specifically, insulin pumps typically deliver insulin in a periodic manner with the period of delivery in the range of 2 to 3 minutes and the duration of delivery at each period being on the order of a few seconds or less. The amount of insulin that is delivered each period may be varied depending on the overall insulin delivery rate that is desired. The analyte data is collected continuously (as, for example, a continuous current of glucose oxidation) but is typically reported to the user periodically. The analyte reporting period is typically 1 to 10 minutes and glucose oxidation current needs to be collected for 10 to 30 seconds in order to generate a reportable glucose value (to allow for filtering etc.).

Indeed, the integration of analyte monitoring and insulin delivery may necessitate placement of a analyte sensor in close proximity to an insulin infusion cannula on the body. Such close proximity engenders the possibility of insulin delivery interfering with the analyte measurements. For example, if insulin infusion should result in a localized decrease in the glucose concentration in the area of the body near the infusion site, then glucose measurement in this area would not be representative of the glucose concentration in the body as a whole. Accordingly, in one embodiment of the present invention, there is provided a method for temporal spacing of blood glucose measurements and insulin delivery to mitigate the possible interference between insulin infusion and glucose measurements.

In accordance with one embodiment, the temporal spacing of analyte measurement and insulin delivery may include providing as large a temporal gap from after insulin delivery and before taking a analyte measurement. Since both analyte measurement and insulin delivery are performed periodically, a maximum spacing in time may be achieved if analyte measurement substantially immediately precedes insulin delivery. During the time between insulin delivery and the subsequent glucose measurement, infused insulin has time to diffuse and be transported away from the infusion site due to normal circulation of interstitial fluid. An example timeline of temporally spaced analyte measurement and insulin delivery is shown in FIG. 13. If multiple analyte measurements are taken between insulin delivery points, there should always be a reading just prior to insulin delivery and as well just after insulin delivery to minimize the affect of injected insulin on the glucose measurement readings.

Although readings are typically taken periodically for simplicity in processing, a reading may be taken out of time with other readings and scaled appropriately for the overall reading average. Similarly, the insulin delivery point may be delayed slightly until after the reading with little or no affect as the readings typically occur much more frequently than the infusions, which are intended to act over longer periods of time. In addition, other timing considerations may be considered depending on the environment in which the integrated infusion device and analyte monitoring system is used by the patient, within the scope of the present invention to minimize potential error on measured analyte levels and/or introduce noise or potential adverse effects to the infusion rates of the infusion device.

More specifically, fluctuation in the power supplies of the infusion device and/or the analyte monitoring system including, for example, batteries or related power distribution circuitry may introduce electrical noise effects which may adversely affect the measured readings associated with the analyte monitoring system. For example, when the analyte monitoring system is configured to be in an active state so as to be transmitting or receiving data, or when the pump cycle of the infusion device is active, the power supply may be affected by the load from the data transmission/reception, or the pumping cycle. The adverse effect of the power supply in addition to noise from other components of the electronic circuitry may introduce undesirable noise and adversely affect the accuracy of the analyte sensor measurements.

Accordingly, the transmitter unit 150 (FIG. 1) for example, may be configured to monitor the timing or occurrence of the measured analyte level received from the analyte sensor 160 and the data transmission timing of the transmitter unit 150 such that the two events do not substantially overlap or occur at substantially the same time. Alternatively, the analyte monitor unit 120 (FIG. 1) may be configured to compare the timing of the analyte sensor 160 measurement and the timing of the data transmission from the transmitter unit 150, and to discard analyte related data received from the transmitter unit 150 which coincide with the timing of the analyte measurements by the analyte sensor 160.

Moreover in one embodiment, air bubble detection in the insulin tubing may be provided, by monitoring fluid motion that would also detect the absence of fluid such as that due to an air bubble in the line. In one embodiment, the flow sensor may be configured to generate zero current when an air bubble is present.

In addition, colorization of insulin may be provided for air bubble detection in the tubing. Since pharmaceutical insulin is a clear colorless liquid, it is difficult to visually discriminate between insulin and air in tubing that carries insulin from the insulin pump to the cannula. By providing a color tint to the insulin it would be much easier to visually identify air bubbles in the tubing and be able to remove them before they cause problems. An insulin tint in one embodiment is biocompatible and insulin compatible.

Accordingly, a system including an infusion device and an analyte monitoring unit in one embodiment of the present invention includes an infusion device, an on-body unit including a data transmission section, the on-body unit further coupled to the infusion device, the on-body unit configured to receive one or more signals corresponding to a respective one or more analyte levels, and further, the on-body unit configured to infuse a fluid received from the infusion device, and a receiver unit operatively coupled to the on-body unit, the receiver unit configured to receive data from the on-body unit, wherein the received data is associated with the analyte level.

The system may further include an analyte sensor at least a first portion of which is in fluid contact with an analyte of a patient, and further, where at a second portion of the analyte sensor is in signal communication with the data transmission section.

The data transmission section may in one embodiment be configured to transmit the one or more signals corresponding to a respective one or more analyte levels substantially periodically at one or more predetermined time intervals, where the one or more predetermined time intervals may include one or more of 30 seconds, one minute, or 90 seconds.

In one aspect, the on-body unit may include a cannula at least a portion of which is subcutaneously positioned under a skin layer, and further, may also include an infusion tubing connected to the infusion device to deliver the fluid to the on-body unit. The infusion tubing and the on-body unit in a further aspect may be connected in a substantially water tight seal.

In yet another embodiment, the infusion tubing may be configured to operatively couple to the cannula to deliver the fluid.

The on-body unit may be configured to wirelessly transmit the one or more signals corresponding to the respective one or more analyte levels to the receiver unit, where the on-body unit and the receiver may be configured to wirelessly communicate over one or more of an RF communication link, a Bluetooth® communication link, or an infrared communication link.

In addition, the infusion device in a further embodiment may be configured to control the delivery rate of the fluid based on the one or more signals corresponding to the respective one or more analyte levels received by the receiver unit, and further, where the infusion device may be configured to determine a modified delivery protocol for delivering fluid such as insulin based on information associated with the one or more signals corresponding to the respective one or more analyte levels.

In yet another aspect, the modified delivery protocol may include one or more of a correction bolus, a modified basal profile, a carbohydrate bolus, an extended bolus, or combinations thereof.

The receiver unit in one embodiment may be configured to wirelessly communicate with the infusion device.

In a further embodiment, the receiver unit maybe integrated into a housing of the infusion device.

A method of integrating analyte monitoring and fluid infusion in another embodiment of the present invention includes infusing a fluid at a predetermined delivery rate, detecting one or more analyte levels, transmitting one or more signals associated with the respective detected one or more analyte levels, and determining a modified delivery rate based on the transmitted one or more signals.

In one aspect, the one or more signals may be transmitted substantially immediately after the associated respective one or more analyte levels are detected.

Moreover, the transmitting step in one embodiment may include wirelessly transmitting the one or more signals which wirelessly transmitted over one or more of an RF communication link, a Bluetooth® communication link, an infrared communication link, or combinations thereof.

The method in a further aspect may also include the steps of receiving the transmitted one or more signals, and displaying the received one or more signals.

Moreover, the method may also include the step of displaying the modified delivery rate. In addition, the method may also include the step of implementing the modified delivery rate, where the predetermined delivery rate may include one or more basal delivery rates.

The modified delivery rate in a further embodiment may include one or more of a correction bolus, a modified basal profile, a carbohydrate bolus, an extended bolus, or combinations thereof.

An apparatus including an analyte sensor and a fluid delivery channel in yet another embodiment of the present invention includes a fluid delivery unit having an inner wall and an outer wall, and a plurality of electrodes disposed between the inner wall and the outer wall of the fluid delivery unit, where a portion of the of the fluid delivery unit and a portion of the plurality of electrodes are subcutaneously positioned under a skin layer.

In one aspect, the plurality of electrodes may comprise an analyte sensor, including, for example, one or more of a working electrode, a counter electrode, a reference electrode, or combinations thereof.

The fluid delivery unit may include a channel for delivering a fluid such as insulin, the channel substantially formed by the inner wall.

An apparatus including an analyte sensor and a fluid delivery channel in accordance with still another embodiment of the present invention includes a first tubing having a first tubing channel, and a second tubing having a second tubing channel including a plurality of electrodes disposed within the second tubing channel, where at least a portion of the first tubing and at least a portion of the second tubing are subcutaneously positioned under a skin layer.

In one embodiment, the plurality of the electrodes may be substantially and entirely insulated from each other.

In another embodiment, the first tubing and the second tubing may be integrally formed such that an outer surface of the first tubing is substantially in contact with an outer surface of the second tubing.

A system including an infusion device and an analyte monitoring unit in accordance with still another embodiment of the present invention includes an infusion and monitoring device, an on-body unit including a data transmission section, the on-body unit further coupled to the infusion and monitoring device, the on-body unit configured to receive one or more signals corresponding to a respective one or more analyte levels, and further, the on-body unit configured to infuse a fluid received from the infusion and monitoring device, and a connector coupled at a first end to the infusion device, and further, coupled at a second end to the on-body unit, the connector configured to channel the fluid from the infusion device to the on-body unit, and further, configured to provide the one or more signals corresponding to the respective one or more analyte levels to the infusion and monitoring device.

In one aspect, the infusion and monitoring device may be configured to execute fluid delivery to a patient, and further, to detect analyte levels of the patient over a predetermined time period.

In a further aspect, the infusion and monitoring device may include a continuous glucose monitoring system.

In still another aspect, the infusion and monitoring device may include an insulin pump.

A method of fluid delivery and analyte monitoring in accordance with still another embodiment of the present invention includes determining a delivery profile for fluid infusion, wherein the delivery profile including a plurality of predetermined discrete fluid infusion each temporally separated by a predetermined time period, and sampling an analyte level substantially immediately prior to each predetermined discrete fluid infusion.

The method may further include the step of sampling an analyte level substantially immediately after each predetermined discrete fluid infusion.

Various other modifications and alternations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. A glucose monitoring device, comprising:
a device housing including a display for outputting one or more of a graphical information or alphanumeric information;
a data communication connection provided in the housing including one or more of a wired communication section or a wireless communication section;
a strip port coupled to the housing and configured to receive an in vitro test strip; and
a controller operatively coupled to the data communication connection and the strip port and provided in the device housing, the controller configured to determine a blood glucose level based on a blood sample on the test strip, the controller further configured to process analyte sensor data corresponding to a monitored analyte level;
wherein the determined blood glucose level or the processed analyte sensor data or both, are output on the display graphically or alphanumerically or based on a combination thereof; and further
wherein the controller is in signal communication with an on-body patch pump via the data communication connection and includes a memory having instructions stored which, when executed by one or more processors, causes the on-body patch pump to deliver a medication based on the delivery profile, wherein the delivery profile includes a plurality of predetermined discrete medication infusions temporally separated by a predetermined time period, and wherein the memory having instructions stored which, when executed by the processor, obtains at least one of the plurality of signals associated with the monitored analyte level substantially immediately prior to the delivery of each of the predetermined discrete medication infusions.

2. The device of claim 1 wherein the wired communication section includes a Universal Serial Bus (USB) connection physically coupled to the device housing, and configured to establish wired data communication to a data processing terminal.

3. The device of claim 2 wherein the determined blood glucose level or the processed analyte sensor data or both are transferred to the data processing terminal based on the USB connection.

4. The device of claim 1 wherein the analyte sensor data is received using the wireless communication section.

5. The device of claim 4 wherein the wireless communication section includes a radio frequency (RF) communication section.

6. The device of claim 1 wherein the controller is configured to communicate with an infusion device via the data communication connection.

7. The device of claim 6 wherein the controller transmits one or more signals to the infusion device to control the delivery rate of a fluid based on the one or more analyte sensor data.

8. The device of claim 7 wherein the fluid is insulin.

9. The device of claim 1 wherein the analyte sensor data includes analyte sensor data received from an in vivo glucose sensor.

10. The device of claim 1 including an input unit provided on the housing to enter one or more input commands to the device.

11. The device of claim 10 wherein the input unit includes one or more of a button or a jog dial.

12. The device of claim 1 wherein the controller is further configured to determine a medication dose.

13. The device of claim 12 wherein the controller is configured to execute the determined medication dose.

14. The device of claim 12 wherein the controller is configured to determine the medication dose based at least in part on the determined blood glucose level or the processed analyte sensor data or both.

15. The device of claim 12 wherein the medication dose is output on the display graphically or alphanumerically or based on a combination thereof.

16. The device of claim 12 wherein the medication dose includes a bolus dose.

17. The device of claim 16 wherein the bolus dose includes a correction bolus, a carbohydrate bolus, an extended bolus, a dual bolus, or one or more combinations thereof.

18. The device of claim 12 wherein the controller determines the medication dose based on one or more of an insulin sensitivity information, insulin on board information, intended carbohydrate intake information, measured glucose level, detected glucose level, or glucose trend information.

19. A device, comprising:
a device housing including a display for outputting one or more of a graphical information or alphanumeric information;
a data communication connection provided in the housing including one or more of a wired communication section or a wireless communication section;
a strip port coupled to the housing and configured to receive an in vitro test strip; and
a controller operatively coupled to the data communication connection and the strip port and provided in the device housing, the controller configured to determine a blood glucose level based on a blood sample on the test strip and to process analyte sensor data corresponding to a monitored analyte level, the controller further configured to determine a medication dose based at least in part on one or more of the determined blood glucose level or the processed analyte sensor data;
wherein one or more of the determined blood glucose level, the processed analyte sensor data, or the determined medication dose, are output on the display graphically or alphanumerically or based on a combination thereof;
wherein the graphical output on the display includes an analyte level trend information; and further
wherein the controller is in signal communication with an on-body patch pump via the data communication connection and includes a memory having instructions stored which, when executed by one or more processors, causes the on-body patch pump to deliver a medication based on the delivery profile, wherein the delivery profile includes a plurality of predetermined discrete medication infusions temporally separated by a predetermined time period, and wherein the memory having instructions stored which, when executed by the processor, obtains at least one of the plurality of signals associated with the monitored analyte level substantially immediately prior to the delivery of each of the predetermined discrete medication infusions.

20. The device of claim 19 wherein the wired communication section includes a Universal Serial Bus (USB) connection physically coupled to the device housing, and configured to establish wired data communication to a data processing terminal.

21. The device of claim 20 wherein the determined blood glucose level or the processed analyte sensor data or both are transferred to the data processing terminal based on the USB connection.

22. The device of claim 19 wherein the analyte sensor data is received using the wireless communication section.

23. The device of claim 22 wherein the wireless communication section includes a radio frequency (RF) communication section.

24. The device of claim 19 wherein the controller is configured to communicate with an infusion device via the data communication connection.

25. The device of claim 24 wherein the controller transmits one or more signals to the infusion device to control the delivery rate of a fluid based on the one or more analyte sensor data.

26. The device of claim 25 wherein the delivery rate of the fluid is related to the determined medication dose.

27. The device of claim 25 wherein the fluid is insulin.

28. The device of claim 19 wherein the analyte sensor data includes analyte sensor data received from an in vivo glucose sensor.

29. The device of claim 19 including an input unit provided on the housing to enter one or more input commands to the device.

30. The device of claim 29 wherein the input unit includes one or more of a button or a jog dial.

31. The device of claim 19 wherein the controller is configured to execute the determined medication dose.

32. The device of claim 19 wherein the medication dose includes a bolus dose.

33. The device of claim 32 wherein the bolus dose includes a correction bolus, a carbohydrate bolus, an extended bolus, a dual bolus, or one or more combinations thereof.

34. The device of claim 19 wherein the controller determines the medication dose based on one or more of an insulin sensitivity information, insulin on board information, intended carbohydrate intake information, measured glucose level, detected glucose level, or glucose trend information.

* * * * *